(12) United States Patent
Strassler et al.

(10) Patent No.: US 7,705,046 B2
(45) Date of Patent: Apr. 27, 2010

(54) CRYSTALLINE FORMS OF PERINDOPRIL ERBUMINE

(75) Inventors: Christoph Strassler, Zurich (CH); Vit Lellek, Zurich (CH); Roger Fassler, Langwiesen (CH)

(73) Assignee: Les Laboratoires Servier, Neuilly sur Seine (FR)

( * ) Notice: Subject to any disclaimer, the term of this patent is extended or adjusted under 35 U.S.C. 154(b) by 181 days.

(21) Appl. No.: 10/560,464

(22) PCT Filed: Jun. 18, 2004

(86) PCT No.: PCT/CH2004/000374

§ 371 (c)(1),
(2), (4) Date: Nov. 28, 2006

(87) PCT Pub. No.: WO2004/113293

PCT Pub. Date: Dec. 29, 2004

(65) Prior Publication Data

US 2007/0135512 A1 Jun. 14, 2007

(30) Foreign Application Priority Data

Jun. 24, 2003 (CH) .................................. 1109/03

(51) Int. Cl.
*A61K 31/405* (2006.01)
*C07D 209/12* (2006.01)

(52) U.S. Cl. .................. 514/515; 514/186; 548/514

(58) Field of Classification Search .................. 514/419; 548/492

See application file for complete search history.

(56) References Cited

U.S. PATENT DOCUMENTS

| | | | |
|---|---|---|---|
| 4,508,729 A | 4/1985 | Vincent et al. | |
| 4,914,214 A | 4/1990 | Vincent et al. | |
| 7,351,840 B2 * | 4/2008 | Rao et al. | ................... 548/515 |
| 2003/0158121 A1 | 8/2003 | Pfeiffer et al. | |
| 2003/0186896 A1 | 10/2003 | Pfeiffer et al. | |
| 2004/0029813 A1 | 2/2004 | Pfeiffer et al. | |
| 2007/0178166 A1 * | 8/2007 | Bernstein et al. | ............. 424/499 |

FOREIGN PATENT DOCUMENTS

| | | |
|---|---|---|
| EP | 0049658 A1 | 4/1982 |
| EP | 0308341 A1 | 3/1989 |
| EP | 1256590 A1 | 11/2002 |
| WO | WO 01/58868 A1 | 8/2001 |
| WO | WO 01/83439 A2 | 11/2001 |
| WO | WO 01/87835 A1 | 11/2001 |
| WO | WO 01/87836 A1 | 11/2001 |
| WO | WO 2004/046172 A1 | 6/2004 |

OTHER PUBLICATIONS

FDA publication on drug ACEON (perindopril erbumine) Tablets Rx, Mar. 2003.*
Wikipedia under Perindopril.*
cardiovascular diseases, WHO web site page.*

* cited by examiner

*Primary Examiner*—Yong Chu
(74) *Attorney, Agent, or Firm*—Hammer & Associates, P.C.

(57) ABSTRACT

Disclosed are two new crystalline forms, δ and ε, of perindopril erbumine. Those forms are suitable as therapeutic active substances for medicaments for the treatment of cardio-vascular diseases, especially high blood pressure and heart failure. The ε crystalline form is obtained in the crystallization of perindopril erbumine at from 30 to 45° C., preferably from 34 to 45° C., from MTBE containing from 1.5 to 2.5% (v/v) water; the crystallization is advantageously carried out with stirring. If the water is then removed, advantageously by azeotropic distillation, preferably at from 35 to 37° C., and stirring is then continued for at least 15 h at from 30 to 45° C., preferably from 35 to 37° C., the ε crystalline form is converted to the δ crystalline form. The δ crystalline form can also be obtained by stirring the α or β crystalline form at from 33 to 38° C. in tert.-butyl methyl ether containing from 0.9 to 1.4% (v/v) water with seeding with the δ crystalline form. The ε crystalline form can also be obtained by stirring the α or β crystalline form at from 28 to 35° C. in tert.-butyl methyl ether containing from 0.9 to 1.4% (v/v) water with seeding with the ε crystalline form; or by stirring the α or β crystalline form at from 35 to 38° C. in tert.-butyl methyl ether containing from 1.5 to 2.0% (v/v) water.

5 Claims, No Drawings

CRYSTALLINE FORMS OF PERINDOPRIL ERBUMINE

RELATED APPLICATION

This application claims the benefit of PCT application Serial Number PCT/CH2004/000374 filed Jun. 18, 2004 which claims the benefit of Swiss application Serial Number 1109 filed Jun. 24, 2003.

The present invention relates to two new crystalline forms of perindopril erbumine.

Perindopril ((2S,3aS,7aS)-1-[2-(1-ethoxycarbonyl-(S)-butylamino)-(S)-propionyl]-octa-hydroindole-2-carboxylic acid) has the following formula (I):

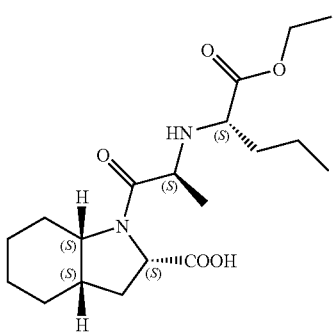

Perindopril erbumine is the tert.-butylamine salt of perindopril.

Perindopril acts as an ACE inhibitor (ACE=angiotensin-converting enzyme) and is used in the treatment of cardiovascular diseases, especially in the treatment of high blood pressure and heart failure.

Processes for the synthesis of perindopril are described in EP 49 658, U.S. Pat. No. 4,508,729, EP 308 341 and U.S. Pat. No. 4,914,214 and also in EP 1 256 590 and WO 01/58868.

In WO 01/87835, WO 01/87836 and WO 01/83439 there are described processes for the crystallisation of perindopril erbumine from ethyl acetate (WO 01/87835), from dichloromethane or ethyl acetate (WO 01/87836) and from chloroform (WO 01/83439), and the α (WO 01/87835), β (WO 01/87836) and γ (WO 01/83439) crystalline forms obtained in those processes.

It has now been found that by crystallisation of perindopril erbumine of any crystalline form from tert.-butyl methyl ether containing from 0.9 to 2.5% v/v water, or by transforming the α or β crystalline form of perindopril erbumine in tert.-butyl methyl ether containing from 0.9 to 2.5% v/v water, two further crystalline forms, δ and ε, can be obtained depending on the precise conditions. Those new δ and ε crystalline forms are characterised by the following X-ray diffraction data (see Tables 1 and 2 below):

TABLE 1

X-ray diffraction data of perindopril erbumine, δ crystalline form (relative intensities were taken from the powder diagram obtained by CuK$_\alpha$ irradiation.

| Angle 2 theta (°) | Lattice spacing d (Å) | Relative intensity I/I$_{max}$ (%) |
|---|---|---|
| 5.27 | 16.79 | 2 |
| 8.93 | 9.93 | 100 |

TABLE 1-continued

X-ray diffraction data of perindopril erbumine, δ crystalline form (relative intensities were taken from the powder diagram obtained by CuK$_\alpha$ irradiation.

| Angle 2 theta (°) | Lattice spacing d (Å) | Relative intensity I/I$_{max}$ (%) |
|---|---|---|
| 9.75 | 9.10 | 32 |
| 10.65 | 8.34 | 10 |
| 14.63 | 6.10 | 25 |
| 14.97 | 5.97 | 39 |
| 15.27 | 5.85 | 48 |
| 15.95 | 5.61 | 53 |
| 17.27 | 5.19 | 18 |
| 17.87 | 5.02 | 15 |
| 18.63 | 4.83 | 13 |
| 19.99 | 4.51 | 29 |
| 20.37 | 4.43 | 26 |
| 21.31 | 4.24 | 57 |
| 21.83 | 4.15 | 37 |
| 22.49 | 4.03 | 26 |
| 23.15 | 3.92 | 19 |
| 23.65 | 3.84 | 29 |
| 23.99 | 3.79 | 16 |
| 24.71 | 3.69 | 15 |
| 25.33 | 3.60 | 15 |
| 25.75 | 3.55 | 15 |
| 26.43 | 3.46 | 21 |
| 26.77 | 3.42 | 18 |
| 28.19 | 3.26 | 24 |

TABLE 2

X-ray diffraction data of perindopril erbumine, ε crystalline form (relative intensities were taken from the powder diagram obtained by CuK$_\alpha$ irradiation).

| Angle 2 theta (°) | Lattice spacing d (Å) | Relative intensity I/I$_{max}$ (%) |
|---|---|---|
| 5.28 | 16.75 | 2 |
| 8.43 | 10.52 | 22 |
| 8.87 | 10.00 | 100 |
| 9.45 | 9.39 | 92 |
| 10.01 | 8.87 | 20 |
| 13.58 | 6.57 | 6 |
| 14.21 | 6.28 | 14 |
| 14.79 | 6.04 | 61 |
| 15.31 | 5.84 | 53 |
| 15.84 | 5.65 | 49 |
| 16.43 | 5.45 | 13 |
| 16.84 | 5.32 | 13 |
| 17.65 | 5.09 | 18 |
| 18.65 | 4.82 | 11 |
| 19.87 | 4.54 | 29 |
| 21.21 | 4.26 | 49 |
| 21.79 | 4.15 | 55 |
| 22.79 | 3.98 | 27 |
| 23.52 | 3.86 | 30 |
| 24.25 | 3.75 | 25 |
| 25.83 | 3.54 | 23 |
| 26.55 | 3.45 | 25 |
| 27.25 | 3.37 | 15 |
| 28.11 | 3.27 | 27 |

Note:
It is well known that the intensities may vary on account of texture effects.

In accordance with the invention, the ε crystalline form is obtained in the crystallisation at from 30 to 45° C., preferably from 34 to 45° C., of perindopril erbumine of any crystalline form from tert.-butyl methyl ether (MTBE) containing from 1.5 to 2.5% v/v water; the crystallisation is advantageously carried out with stirring. If the water is then removed, advantageously by azeotropic distillation, preferably at from 35 to 37° C., and stirring is then continued for at least 15 h at from 30 to 45° C., preferably from 35 to 37° C., the ε crystalline form is converted to the δ crystalline form.

In addition, the α and β crystalline forms of perindopril erbumine, which are already known, can be converted to the δ crystalline form by stirring at from 33 to 38° C., preferably from 35 to 37° C., in tert.-butyl methyl ether (MTBE) containing from 0.9 to 1.4% v/v water, preferably from 1.0 to 1.1% v/v water, and seeding with the δ crystalline form.

In tert.-butyl methyl ether (MTBE) containing from 0.9 to 1.4% v/v water, preferably from 1.0 to 1.1% v/v water, the already known α and β forms can be converted to the ε crystalline form at from 28 to 35° C., preferably from 31 to 33° C., by seeding with the ε crystalline form.

Those conversions can also be carried out without seeding, but in the boundary region it cannot, of course, be predicted with certainty whether the δ form, the ε form or mixtures of those forms will be obtained.

The conversion of the α and β crystalline forms to the ε crystalline form can also be carried out at from 35 to 38° C. in tert.-butyl methyl ether (MTBE) containing from 1.5 to 2.0% v/v water.

Both δ and ε crystalline forms of perindopril erbumine are new and the present invention relates thereto.

They can be used in accordance with the invention as therapeutic active substances and processed together with a pharmaceutically acceptable carrier material to form a medicament. The medicament can then be used in the treatment of cardiovascular diseases, especially in the treatment of high blood pressure and heart failure.

Pharmaceutically acceptable carrier materials for the preparation of medicaments are generally known and are familiar to the person skilled in the art.

Since different forms of a pharmaceutical active substance, such as, for example, new crystalline forms, generally exhibit different bioavailabilities, solubilities and dissolution rates, they may be of great advantage for the relevant patients since they may make it possible for the dose to be reduced or for the dosage intervals to be increased, and consequently for the costs of the medicament to be reduced.

The following Examples are intended to illustrate the invention but not to limit the invention in any way in its scope and its use:

The X-ray diffraction spectra were measured on a Philips ADP1700 powder diffractometer with a Cu irradiation of $K_{\alpha 1}=0.15406$ nm and $K_{\alpha 2}=0.15444$ and a voltage of 40 kV.

EXAMPLE 1

ε Crystalline Form of Perindopril Erbumine 5.00 g of perindopril erbumine were suspended in 50 ml of MTBE and 0.95 ml of water was added. The suspension obtained was heated, with stirring, to 48° C., a clear solution being formed. The solution was cooled, with stirring, to 41° C. Seeding was carried out at that temperature, after which crystallisation commenced. Stirring was carried out for 30 min. at from 40 to 41° C. and then the mixture was cooled to 34° C. in the course of 1 h. The resulting precipitate was filtered off and washed with 10 ml of MTBE. After drying, 1.85 g of perindopril erbumine of the ε crystalline form were obtained.

EXAMPLE 2

β Crystalline Form of Perindopril Erbumine 11.09 g of perindopril erbumine were suspended in 130 ml of MTBE and 2 ml of water were added. The suspension obtained was heated, with stirring, to 51° C., a clear solution being formed. The solution was cooled to 35° C. in the course of 120 min., with stirring. Seeding was carried out at 44° C., after which crystallisation commenced. At from 35 to 37° C., 50 ml of MTBE were distilled off under reduced pressure in the course of 45 min. At the same time the water was also removed azeotropically. 50 ml of MTBE were then added again and, at from 35 to 37° C., 50 ml of MTBE were distilled off again, under reduced pressure, in the course of 60 min. Stirring was continued at from 35 to 37° C. for 15 h, and then the precipitate obtained was filtered off and washed with 10 ml of MTBE. After drying, 8.42 g of perindopril erbumine of the δ crystalline form were obtained.

EXAMPLE 3

Conversion of the α Crystalline Form to the δ Crystalline Form 8.50 g of perindopril erbumine of the α crystalline form were suspended in 85 ml of MTBE and the suspension was heated, with stirring, to from 35 to 37° C. 0.85 ml of water was added thereto, followed by 0.17 g of seed crystals of the δ crystalline form. The suspension obtained was stirred for 23 h at from 35 to 37° C. and then the precipitate was filtered off. After drying, 7.00 g of the δ crystalline form were obtained.

EXAMPLE 4

Conversion of the α Crystalline Form to the ε Crystalline Form 21.66 g of perindopril erbumine of the α crystalline form were suspended in 216 ml of MTBE and the suspension was heated, with stirring, to from 33 to 35° C. 2.16 ml of water were added thereto and the suspension obtained was stirred for 14 h at from 33 to 35° C.

After filtering off and drying the precipitate, 18.68 g of the ε crystalline form were obtained.

EXAMPLE 5

Conversion of the β Crystalline Form to the δ Crystalline Form 4.00 g of perindopril erbumine of the β crystalline form were suspended in 40 ml of MTBE and 0.36 ml of water was added. The suspension obtained was heated to from 35 to 37° C. and stirred for 20 h at from 35 to 37° C. After filtering off and drying the precipitate, the δ crystalline form was obtained.

EXAMPLE 6

Conversion of the α Crystalline Form to the ε Crystalline Form 7.55 g of perindopril erbumine of the α crystalline form were suspended in 75 ml of MTBE and the suspension was heated, with stirring, to from 35 to 37° C. 1.32 ml of water were added thereto and the suspension obtained was stirred for 20 h at from 35 to 37° C. After filtering off and drying the precipitate, 2.31 g of the ε crystalline form were obtained.

The invention claimed is:

1. δ crystalline form of perindopril erbumine, characterised by the following X-ray diffraction data (measured on a powder diffractometer with $CuK_\alpha$ irradiation):

| Angle 2 theta (°) | Lattice spacing d (Å) | Relative intensity $I/I_{max}$ (%) |
|---|---|---|
| 5.27 | 16.79 | 2 |
| 8.93 | 9.93 | 100 |
| 9.75 | 9.10 | 32 |
| 10.65 | 8.34 | 10 |
| 14.63 | 6.10 | 25 |
| 14.97 | 5.97 | 39 |
| 15.27 | 5.85 | 48 |
| 15.95 | 5.61 | 53 |
| 17.27 | 5.19 | 18 |
| 17.87 | 5.02 | 15 |
| 18.63 | 4.83 | 13 |
| 19.99 | 4.51 | 29 |
| 20.37 | 4.43 | 26 |
| 21.31 | 4.24 | 57 |
| 21.83 | 4.15 | 37 |
| 22.49 | 4.03 | 26 |
| 23.15 | 3.92 | 19 |
| 23.65 | 3.84 | 29 |
| 23.99 | 3.79 | 16 |
| 24.71 | 3.69 | 15 |
| 25.33 | 3.60 | 15 |
| 25.75 | 3.55 | 15 |

-continued

| Angle 2 theta (°) | Lattice spacing d (Å) | Relative intensity $I/I_{max}$ (%) |
|---|---|---|
| 26.43 | 3.46 | 21 |
| 26.77 | 3.42 | 18 |
| 28.19 | 3.26 | 24. |

2. Medicaments, containing a crystalline form of perindopril erbumine according to claim 1.

3. A solid pharmaceutical composition comprising as active ingredient the compound according to claim 1, in combination with one or more pharmaceutically acceptable, inert, non-toxic carriers.

4. The solid pharmaceutical composition according to claim 3 for use as ACE inhibitor in the treatment of hypertension, stable coronary artery disease, and heart failure.

5. Process for the preparation of perindopril erbumine of the δ crystalline form according to claim 1, characterised in that
   a) perindopril erbumine of any crystalline form is recrystallised at from 30 to 45° C. from tert-butyl methyl ether containing from 1.5 to 2.5% (v/v) water, and the precipitate obtained is stirred for at least 15 hours at from 30 to 45° C. after the removal of water; or
   b) perindopril erbumine of the α or β crystalline form is stirred at from 33 to 38° C. in tert.-butyl methyl ether containing from 0.9 to 1.4% (v/v) water with seeding with the δ crystalline form.

* * * * *